(12) United States Patent
Fredrickson et al.

(10) Patent No.: US 12,150,874 B2
(45) Date of Patent: Nov. 26, 2024

(54) MEDICAL DEVICES FORMED FROM POLYMER FILAMENTS

(71) Applicant: BOSTON SCIENTIFIC SCIMED, INC., Maple Grove, MN (US)

(72) Inventors: Gerald Fredrickson, Westford, MA (US); Mark W. Boden, Harrisville, RI (US); Emma Boutcher, Burlington, VT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 941 days.

(21) Appl. No.: 17/175,965

(22) Filed: Feb. 15, 2021

(65) Prior Publication Data

US 2021/0161690 A1 Jun. 3, 2021

Related U.S. Application Data

(63) Continuation of application No. 15/852,334, filed on Dec. 22, 2017, now Pat. No. 10,966,848.

(Continued)

(51) Int. Cl.
*A61F 2/90* (2013.01)
*A61F 2/82* (2013.01)
(Continued)

(52) U.S. Cl.
CPC .................. *A61F 2/90* (2013.01); *A61F 2/82* (2013.01); *A61L 27/14* (2013.01); *A61L 31/041* (2013.01);
(Continued)

(58) Field of Classification Search
CPC ........ A61F 2/90; A61F 2/82; A61F 2250/003; A61L 27/14; A61L 31/041; A61L 31/06;
(Continued)

(56) References Cited

U.S. PATENT DOCUMENTS 5,674,286 A * 10/1997 D'Alessio .............. A61B 17/80
623/1.38
5,705,181 A 1/1998 Cooper et al.
(Continued)

FOREIGN PATENT DOCUMENTS

| CA | 2733182 A1 | 8/2004 |
|----|------------|--------|
| CN | 104640903 A | 5/2015 |

(Continued)

OTHER PUBLICATIONS

International Search Report and Written Opinion dated Apr. 20, 2018 for International Application No. PCT/US2017/068162.
(Continued)

*Primary Examiner* — Paul B Prebilic
(74) *Attorney, Agent, or Firm* — Seager, Tufte & Wickhem, LLP

(57) ABSTRACT

Medical devices and method for manufacturing medical devices are discloses. An example medical device may include a medical device body formed from one or more multi-melting point polymeric filaments. Each of the filaments may include a polymeric blend comprising a first block polymer and a second polymer. The polymeric blend may have a first melting point and a second melting point less than the first melting point. The medical device body may be heat set at a temperature within 10° C. of the second melting point.

19 Claims, 2 Drawing Sheets

Related U.S. Application Data

(60) Provisional application No. 62/440,229, filed on Dec. 29, 2016.

(51) Int. Cl.

| | | |
|---|---|---|
| *A61L 27/14* | (2006.01) | |
| *A61L 31/04* | (2006.01) | |
| *A61L 31/06* | (2006.01) | |
| *D01D 5/00* | (2006.01) | |
| A61L 29/04 | (2006.01) | |
| A61L 31/14 | (2006.01) | |
| C08L 67/04 | (2006.01) | |

(52) U.S. Cl.
    CPC ............... *A61L 31/06* (2013.01); *D01D 5/00* (2013.01); *A61F 2250/0031* (2013.01); *A61L 29/04* (2013.01); *A61L 31/148* (2013.01); *C08L 67/04* (2013.01)

(58) Field of Classification Search
    CPC ............... A61L 31/148; A61L 2430/20; A61L 2430/22; A61L 2400/00
    See application file for complete search history.

(56) References Cited

U.S. PATENT DOCUMENTS

| | | | |
|---|---|---|---|
| 6,245,103 B1* | 6/2001 | Stinson | A61L 31/06 623/1.22 |
| 6,284,333 B1* | 9/2001 | Wang | A61L 29/126 604/95.01 |
| 6,547,819 B2 | 4/2003 | Strecker | |
| 6,663,664 B1 | 12/2003 | Pacetti | |
| 6,869,443 B2 | 3/2005 | Buscemi et al. | |
| 7,011,678 B2 | 3/2006 | Tenerz et al. | |
| 7,410,498 B2 | 8/2008 | Penhasi | |
| 7,455,687 B2 | 11/2008 | Saunders et al. | |
| 7,651,527 B2 | 1/2010 | Krivoruchko et al. | |
| 7,842,737 B2 | 11/2010 | Wang et al. | |
| 7,897,224 B2 | 3/2011 | Thatcher et al. | |
| 7,956,100 B2 | 6/2011 | Wang | |
| 8,012,196 B2 | 9/2011 | Smith et al. | |
| 8,100,963 B2 | 1/2012 | Roth et al. | |
| 8,172,897 B2 | 5/2012 | Gale et al. | |
| 8,192,481 B2 | 6/2012 | King | |
| 8,293,261 B2 | 10/2012 | Nagura | |
| 8,414,635 B2 | 4/2013 | Hyodoh et al. | |
| 8,636,792 B2 | 1/2014 | Zheng et al. | |
| 8,740,973 B2 | 6/2014 | Furst et al. | |
| 8,870,945 B2 | 10/2014 | Dave et al. | |
| 8,876,880 B2 | 11/2014 | Hyodoh et al. | |
| 8,900,619 B2 | 12/2014 | Ranade et al. | |
| 8,998,978 B2 | 4/2015 | Wang | |
| 9,072,820 B2 | 7/2015 | Gale et al. | |
| 9,314,551 B2 | 4/2016 | Atanasoska et al. | |
| 9,468,704 B2 | 10/2016 | Gerold | |
| 9,517,149 B2 | 12/2016 | Gale et al. | |
| 9,655,752 B2 | 5/2017 | Shanov et al. | |
| 9,700,652 B2 | 7/2017 | Loeffler et al. | |
| 2001/0012960 A1 | 8/2001 | Acciai et al. | |
| 2002/0016596 A1* | 2/2002 | Cooper | A61L 27/18 606/77 |
| 2003/0114919 A1 | 6/2003 | McQuiston et al. | |
| 2003/0134099 A1* | 7/2003 | Barrows | C08L 67/04 428/297.4 |
| 2003/0153971 A1 | 8/2003 | Chandrasekaran | |
| 2004/0106988 A1 | 6/2004 | Summers | |
| 2005/0070996 A1 | 3/2005 | Dinh et al. | |
| 2006/0287715 A1 | 12/2006 | Atladottir et al. | |
| 2007/0043434 A1 | 2/2007 | Meerkin et al. | |
| 2007/0250157 A1 | 10/2007 | Nishide et al. | |
| 2008/0051873 A1 | 2/2008 | Cottone et al. | |
| 2008/0069858 A1 | 3/2008 | Weber | |
| 2008/0221670 A1 | 9/2008 | Clerc et al. | |
| 2010/0021550 A1 | 1/2010 | Li et al. | |
| 2010/0082093 A1 | 4/2010 | Weber | |
| 2011/0160839 A1 | 6/2011 | Weber et al. | |
| 2012/0277844 A1 | 11/2012 | Wu | |
| 2014/0353877 A1 | 12/2014 | Wang et al. | |
| 2015/0182674 A1 | 7/2015 | Schaffer | |
| 2015/0282922 A1 | 10/2015 | Hingston et al. | |
| 2016/0058585 A1 | 3/2016 | Seddon et al. | |
| 2017/0021064 A1 | 1/2017 | Gale et al. | |

FOREIGN PATENT DOCUMENTS

| | | |
|---|---|---|
| JP | 2167156 A | 6/1990 |
| JP | 8208966 A | 8/1996 |
| JP | 2000139967 A | 5/2000 |
| JP | 2010515493 A | 5/2010 |
| JP | 201342914 A | 3/2013 |
| JP | 2013144009 A | 7/2013 |
| JP | 2016163619 A | 9/2016 |
| WO | 2013003644 A1 | 1/2013 |
| WO | 2013138086 A1 | 9/2013 |
| WO | 2016114216 A1 | 7/2016 |

OTHER PUBLICATIONS

Gupta et al., "Preparation of Poly(e-caprolactone)/Poly(e-caprolactone-co-lacitide) (PCL/PLCL) Blend Filament by Melt Spinning," Journal of Applied Polymer Science, 123: 1944-1950, 2012.

* cited by examiner

MEDICAL DEVICES FORMED FROM POLYMER FILAMENTS

CROSS-REFERENCE TO RELATED APPLICATIONS

This application is a continuation of U.S. application Ser. No. 15/852,334, filed Dec. 22, 2017, now U.S. Pat. No. 10,966,848, which claims priority to U.S. Provisional Application Ser. No. 62/440,229, filed Dec. 29, 2016, the entirety of which is incorporated herein by reference.

TECHNICAL FIELD

The present disclosure pertains to medical devices, and methods for manufacturing medical devices. More particularly, the present disclosure pertains to medical devices formed from polymer filaments.

BACKGROUND

A wide variety of intracorporeal medical devices have been developed for medical use, for example, intravascular use. Some of these devices include stents, guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example method for manufacturing a medical device is disclosed. The method comprises: forming a multi-melting point filament, wherein the filament includes a blend of a first polymer and a second polymer; wherein the filament includes a first melting point and a second melting point lower than the first melting point; forming the filament into an implantable medical device; and heat setting the filament at a temperature within 10° C. of the second melting point.

Alternatively or additionally to any of the embodiments above, the first polymer includes a block polymer.

Alternatively or additionally to any of the embodiments above, the first polymer includes a block polymer of poly(glycolic acid) and polycaprolactone.

Alternatively or additionally to any of the embodiments above, the first polymer includes a block polymer of poly-L-lactic acid and polycaprolactone.

Alternatively or additionally to any of the embodiments above, the block polymer includes about 60% or more of poly-L-lactic acid.

Alternatively or additionally to any of the embodiments above, the block polymer includes about 70% or more of poly-L-lactic acid.

Alternatively or additionally to any of the embodiments above, the second polymer includes polycaprolactone.

Alternatively or additionally to any of the embodiments above, the first polymer includes a biodegradable polymer.

Alternatively or additionally to any of the embodiments above, the implantable medical device includes a stent.

Alternatively or additionally to any of the embodiments above, forming the filament into an implantable medical device includes weaving, knitting, braiding, or combinations thereof.

Alternatively or additionally to any of the embodiments above, forming a multi-melting point filament includes extruding the blend of the first polymer and the second polymer.

Alternatively or additionally to any of the embodiments above, extruding includes extruding at a temperature at or above the first melting point.

A medical device is disclosed. The medical device comprises: a medical device body formed from one or more multi-melting point polymeric filaments; wherein each of the filaments includes a polymeric blend comprising a first block polymer and a second polymer; wherein the polymeric blend has a first melting point and a second melting point less than the first melting point; wherein the medical device body is heat set at a temperature within 10° C. of the second melting point.

Alternatively or additionally to any of the embodiments above, the first block polymer includes a block polymer of poly-L-lactic acid and polycaprolactone.

Alternatively or additionally to any of the embodiments above, the second polymer includes polycaprolactone.

Alternatively or additionally to any of the embodiments above, the first block polymer includes about 70% or more of poly-L-lactic acid.

Alternatively or additionally to any of the embodiments above, the first block polymer is biodegradable.

Alternatively or additionally to any of the embodiments above, the one or more multi-melting point polymeric filaments are woven, knit, braided, or combinations thereof.

Alternatively or additionally to any of the embodiments above, the medical device body includes a plurality of multi-melting point polymeric filaments.

A stent is disclosed. The stent comprises: a cylindrical body formed from a plurality of woven polymeric filaments; wherein each of the plurality of woven polymeric filaments include a polymeric blend comprising a first block polymer and a second polymer; wherein the polymeric blend has a first melting point and a second melting point lower than the first melting point; wherein the first block polymer comprises poly-L-lactic acid and polycaprolactone; wherein the second polymer comprises polycaprolactone; and wherein the cylindrical body is heat set at a temperature within 10° C. of the second melting point.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
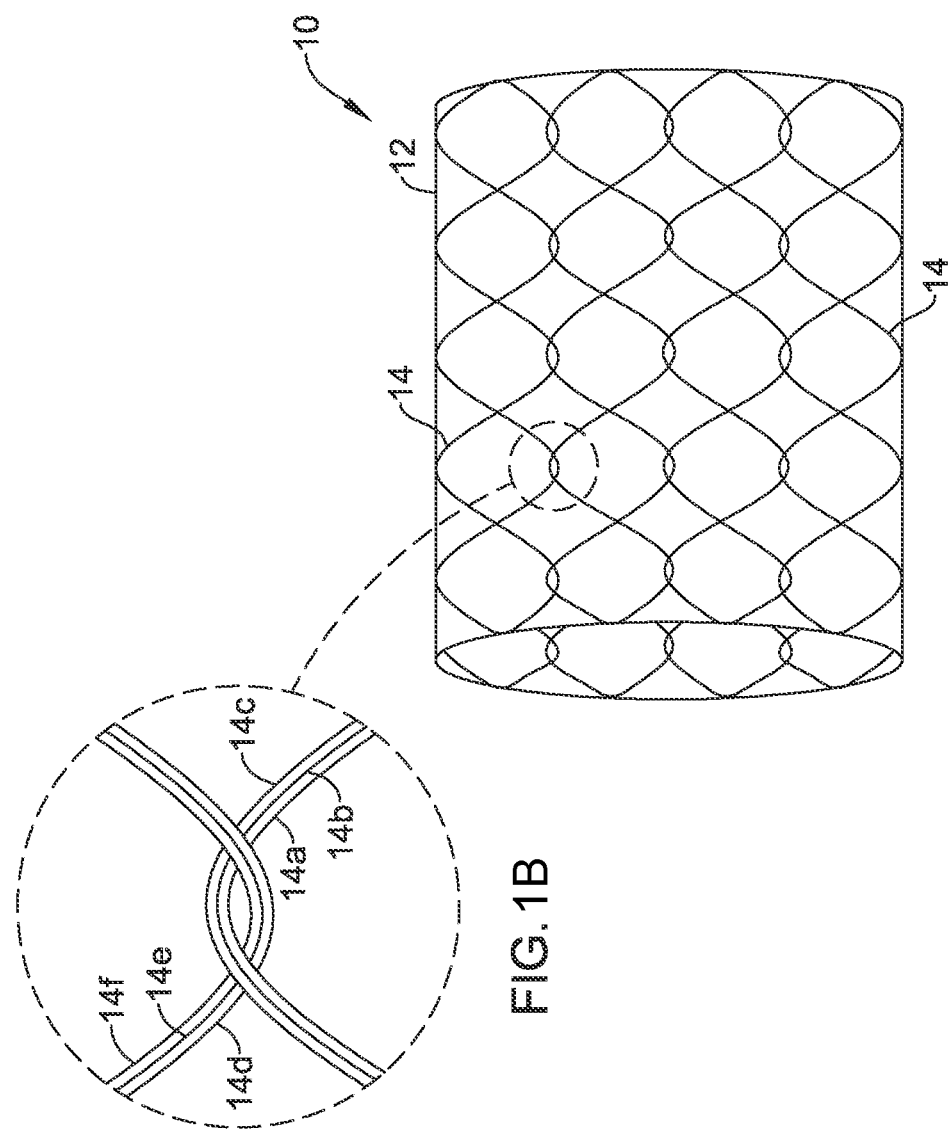
FIG. 1A is a side view of an example medical device and FIG. 1B is closeup view of a portion of FIG. 1A.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1A illustrates an example medical device 10. In this example, the medical device 10 is illustrated as an implantable medical device such as a stent that may be configured to be positioned in a body lumen for any one of a variety of medical applications. For example, the implantable medical device 10 may be used to treat a stenosis in a blood vessel, used to maintain a fluid opening or pathway in the vascular, urinary, biliary, tracheobronchial, esophageal, gastrointestinal, or renal tracts, or position a device such as an artificial valve or filter within a body lumen, in some instances. In some instances, the implantable medical device 10 may be a prosthetic graft, a stent-graft, or a stent (e.g., a vascular stent, tracheal stent, bronchial stent, esophageal stent, etc.), an aortic valve, filter, etc. Although illustrated as a stent, the implantable medical device 10 may be any of a number of devices that may be introduced endoscopically, subcutaneously, percutaneously or surgically to be positioned within an organ, tissue, or lumen, such as a heart, artery, vein, urethra, esophagus, trachea, colon, intestine, bronchus, bile duct, or the like.

The implantable medical device 10 may include a body 12. In some instances, the body 12 is generally cylindrical with a lumen or passageway extending therethrough. This is not intended to be limiting. The form, configuration, shape, etc. of the body 12 can vary. For example, the body 12 may have a generally cylindrical shape along a central portion and may have one or more flared or enlarged end regions. In some of these and in other instances, the body 12 may include two or more lumens or passageways. Numerous other shapes, configurations, etc. are contemplated.

For a variety of reasons it may be desirable to form the body 12 of the implantable medical device 10, or a component thereof, from one or more polymeric filaments 14. For example, the body 12 of the implantable medical device 10 may be formed from a single interwoven polymeric filament 14. Alternatively, the body of the implantable medical device 10 may be formed from a plurality of interwoven polymeric filaments 14. The one or more polymeric filaments may be formed into the implantable medical device 10, such as the tubular body 14 of the medical device 10, using a suitable process such as weaving, knitting, braiding, winding, or the like, or combinations thereof. The number of polymeric filaments 14 utilized to form the implantable medical device 10 may vary. For example, FIG. 1B depicts six polymeric filaments $14a/14b/14c/14d/14e/14f$. However, this is not intended to be limiting. Implantable medical devices are contemplated that include 1, 2, 3, 4, 5, 6, 7, 8, 9, 10, 11, 12, or more polymeric filaments 14.

The use of polymeric filaments 14 allows for devices to be formed that can have a variety of different shapes in multiple dimensions that may prove more challenging to form using other materials/techniques. In at least some instances, it may be desirable for the polymeric filaments 14 to have properties that can provide desirable properties and/or features to the implantable medical device 10. For example, in some instances the implantable medical device 10 may take the form of a tubular stent. It may be desirable for the stent to have a suitable amount of strength in order to reduce breakage of the stent. It may also be desirable for the stent to be heat set into a desired "open" and/or radially expanded shape in order to maintain a fluid opening or pathway in a body lumen. It may also be desirable for the stent to include one or more biodegradable materials. Balancing these and other features may result in an improved stent (e.g., an improved implantable medical device 10). Disclosed herein are implantable medical devices (e.g., the implantable medical device 10) and methods for manufacturing medical devices that have such desirable features and/or other desirable features. At least some of the contemplated medical devices are formed from or otherwise include one or more polymeric filaments. The features of the devices formed from these polymeric filaments may include a desirable amount of strength, a desirable ability to take and hold a shape set (e.g., a heat set), biodegradability, other desirable features, or combinations thereof.

In at least some instances, the polymeric filaments may be formed from a blend of two or more materials. For example, the polymeric filaments may include a polymer blend comprising a first polymer or polymer block and a second polymer or polymer block. In at least some instances, the first polymer/block, the second polymer/block, or both include a biodegradable or bioabsorbable material. Such materials may allow the resultant implantable medical device 10 to be deployed within a body lumen and then slow degrade, absorb or disintegrate over time. In addition, this may allow the implantable medical 10 to be removed.

A number of different polymer blends (e.g., blends of the first polymer/block and the second polymer/block) are contemplated. For example, the first polymer may be a block polymer including poly-L-lactic acid (PLLA) and poly-caprolactone (PCL) monomers. The second polymer may include PCL. In some instances, the first polymer block may include about 50% or more PLLA (e.g., about 50% or more of the monomers in the first polymer block are PLLA), or about 60% or more PLLA (e.g., about 60% or more of the monomers in the first polymer block are PLLA), or about 70% or more PLLA (e.g., about 70% or more of the monomers in the first polymer block are PLLA), or about 80% or more PLLA (e.g., about 80% or more of the monomers in the first polymer block are PLLA), or about 50-80% PLLA (e.g., about 50-80% of the monomers in the first polymer block are PLLA), or about 60-80% PLLA (e.g., about 60-80% of the monomers in the first polymer block are PLLA), or about 70% PLLA (e.g., about 70% of the monomers in the first polymer block are PLLA).

The polymer blend forming the filament 14 may be a multi-melting point polymer blend. In other words, the blended material may have a first melting point (e.g., a first temperature at which at least a portion of the polymer blend melts) and a second melting point (e.g., a second temperature at which at least a portion of the polymer blend melts) lower than the first melting point. Using differential scanning calorimetry (DSC), it has been determined that varying the composition of polymer blend, more particularly the relative proportions of the monomers making up the first polymer/block, results in greater portions of the polymer blend melting at the second melting point, and thus fewer portions of the polymer blend melting at the first melting point. For example, in polymer blends that include PLLA-PCL as the first polymer/block and PCL as the second polymer, only the first melting point is observed via DSC when only the first polymer/block is analyzed (e.g., the first polymer/block is substantially 100% of the polymer blend). In this example, the first melting point occurs at a temperature between 150-175° C. (e.g., about 162-167° C.). However, the first melting point may vary when other materials are utilized. A portion of a polymer blend that includes 95% PLLA-PCL and 5% PCL has a second melting point. In this example, the second melting point occurs at a temperature between 50-75° C. (e.g., about 53-57° C., or about 55° C.). A relatively small portion of this polymer blend melts at the second melting point. A portion of a polymer blend that includes 90% PLLA-PCL and 10% PCL also has the second melting point. The amount of this polymer blend (i.e., 90% PLLA-PCL and 10% PCL) that melts at the second melting point is greater than the amount melting at the second melting point for the polymer blend that includes 95% PLLA-PCL and 5% PCL. A portion of a polymer blend that includes 80% PLLA-PCL and 20% PCL also has the second melting point. The amount of this polymer blend (i.e., 80% PLLA-PCL and 20% PCL) that melts at the second melting point is greater than the amount melting at the second melting point for the polymer blend that includes 90% PLLA-PCL and 10% PCL. A portion of a polymer blend that includes 70% PLLA-PCL and 30% PCL also has the second melting point. The amount of this polymer blend (i.e., 70% PLLA-PCL and 30% PCL) that melts at the second melting point is greater than the amount melting at the second melting point for the polymer blend that includes 80% PLLA-PCL and 20% PCL.

Without wishing to be bound by theory, highly oriented, high strength and/or highly crystalline polymeric filaments may be used to form a medical device. However, such polymeric filaments may have a relatively small amount of amorphous regions. Because of this, when melting or partially melting these filaments in order to shape set (e.g., heat set) a medical device into the desired shape, relatively few "new" or "additional" crystalline regions may be formed. Accordingly, while the material may be relatively high in strength, it may be challenging to sufficiently heat set the material into a desirable shape and suitably hold the desired shape. In the case of forming a stent, a stent formed from highly oriented, high strength and/or highly crystalline polymeric filaments may have desirable strength characteristics (e.g., strength in tension and/or compression) but may have a lower ability to hold a heat set shape. Thus, such stents implanted in a body lumen may not completely open or radially expand during deployment, may not maintain a desired open or expanded shape, may not retain the desired expanded shape/size, etc.

The use of a polymer blend with multiple melting points may allow for the formation of filaments with desirable characteristics and, thus, the formation of medical devices (e.g., the implantable medical device 10) with desirable characteristics. For example, the higher melting point allows for the formation of the high modulus, high strength, highly oriented polymeric filaments. In other words, the process of forming polymeric filaments where the polymeric material (i.e., polymeric blend) is melted above the first or higher melting point, allows for the formation of highly oriented, high strength and/or highly crystalline polymeric filaments (e.g., the polymeric filaments 14). However, because the polymer blends disclosed herein also have an additional, lower melting point, the polymeric filaments 14 can be formed into a medical device (e.g., the implantable medical device 10) and then heat set at a temperature that is at or near the lower melting point (but lower than the first melting point). For example, the heat setting process can induce a suitable amount of crystallization in the polymeric material such that the medical device (e.g., the implantable medical device 10) can have desirable strength for holding the shape of the heat set by rearranging the amorphous regions in the highly oriented polymeric filaments 14. In other words, the heat set process can utilize the lower melting point to induce further orientation/crystallization in the polymeric filaments 14 such that the resultant medical device (e.g., the implantable medical device 10) can better hold the desired shape. In the case of stent formation, this can lead to the formation of stents that open more fully when deployed, hold their size/shape, etc. In at least some instances, the heat setting occurs at a temperature that is at or near the second melting point, within 5° C. of the second melting point, within 10° C. of the second melting point, or within 20° C. of the second melting point. Generally, the heat setting may occur at a temperature that is below the first or higher melting point of the polymer blend. Finally, it may be desirable to heat set at a temperature that is above the use temperature of the implantable medical device 10. For example, it may be desirable to heat set the implantable medical device at a temperature above body temperature (i.e., above 37° C.).

A number of additional polymer blends are contemplated that may have multiple melting points and, thus, can be utilized in a similar manner. For example, in some instances the first polymer/block is a block polymer comprising PLLA and poly(glycolic acid) (PGA). In at least some of these embodiments, the second polymer is PCL. In another example, the first polymer/block includes polyvinyl acetate (PVA) and/or block polymers that utilize PVA. Suitable PVA polymers may be relatively small (e.g., on the order of about 30,000 Daltons or smaller, or about 20,000 Daltons or smaller, or about 10,000 Daltons or smaller). Additional examples may utilize polydioxanone, poly butyl succinate, trimethylene carbonate, poly(esteramides), poly(tyrosine) esters and carbonates, modified poly(ethylene terephthalate) (e.g., BIOMAX), polyester urethanes, polyanhydrides, combinations thereof, or the like for the first polymer/block, the second polymer/block, or both. In further examples, the first polymer/block, the second polymer/block, or both may include a water soluble polymer such as poly-ethylene oxide (PEO). In still further examples, the first polymer/block, the second polymer/block, or both may include semicrystalline polymers such as nylon blended with a biodegradable polymer (e.g., including those disclosed herein). In still further examples, two amorphous polymers can be blended. One of the amorphous polymers may have relatively low glass transition temperature and another may have a relatively high glass transition temperature. This may allow the implantable medical device 10 to be shape set with the lower glass transition temperature polymer while the higher glass transition temperature polymer may hold the polymer in the original filament or other shape (e.g., and/or provide strength).

In some instances, the implantable medical device 10 may include a coating. In one or more embodiments, the coating includes a biocompatible polymer. In one or more embodiments, the coating includes a bioabsorbable polymer such as a bioabsorbable elastomer. In one or more embodiments, a coating may include one or more therapeutic agents (e.g., embedded therein, coated thereon, etc.). Some example therapeutic agents may include, but are not limited to, angiopeptin, paclitaxel, everolimus, dexamethasone, methyl prednisolone, zotarolimus, estradiol, batimastat, or the like.

Figure 2:
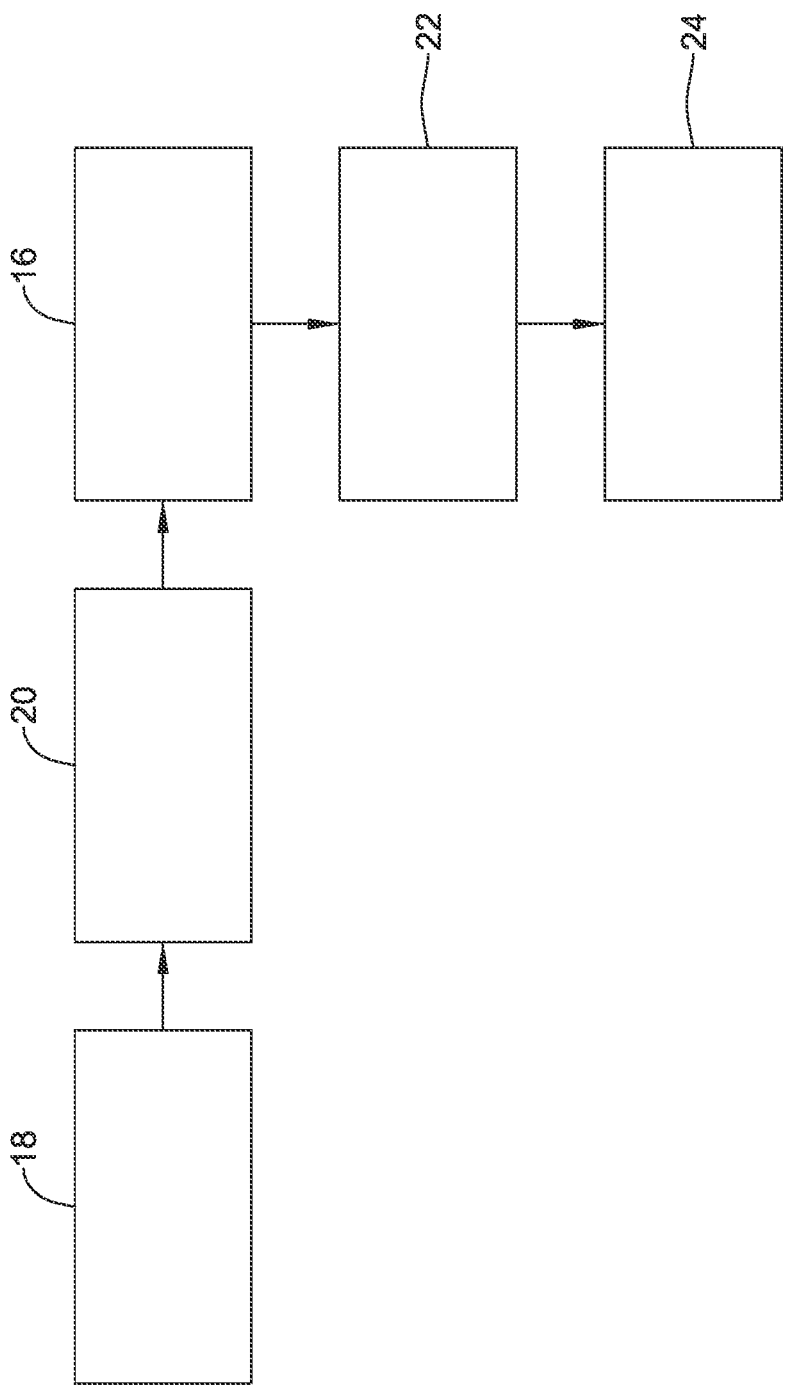
FIG. 2 is a block diagram of an example manufacturing method.

Some of the methods for forming the polymeric filaments 14 and/or the implantable medical devices 10 disclosed herein is schematically represented in FIG. 2 as a flow chart. Box 16 may represent forming the polymeric filaments 14. In some instances, forming the polymeric filaments 14 may include blending the first polymer/block and the second polymer/block (represented at box 18) and processing the polymer blend (e.g., using extrusion or another suitable process), which is represented at box 20. In some instances, the polymeric filaments 14 may be extruded in a number of different shapes (e.g., different linear shapes) and/or post-formed into a number of different complex shapes. The forming process may include orienting/crystallizing the polymeric filaments 14 by melting the polymeric material at a temperature above the first melting point. In other words, part of forming the filaments 14 may include extruding the polymeric material at or above the first melting point to align the polymer chains. This may also include cooling the extruded article (e.g., the filament 14) to allow the polymeric material to crystalize. The resultant filament 14 may be formed of the blend of the first polymer/block and the second polymer/block as disclosed herein. In addition, the filament may have a first melting point and a second melting point as disclosed herein.

The filaments 14 may be formed into the implantable medical device 10 (represented at box 22). This may include weaving, knitting, braiding, or the like. The implantable medical device 10 may then be shape set (e.g., heat set) at a temperature that is near the second melting point. This may include heat setting the implantable medical device that is at or near the second melting point, within 5° C. of the second melting point, within 10° C. of the second melting point, or within 20° C. of the second melting point. For example, if the second melting point is approximately 55° C., it may be desirable to heat set at a temperature of about 55° C.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device, comprising:
    a medical device body formed from one or more multi-melting point polymeric filaments;
    wherein each of the filaments is formed of a polymeric blend of a first block polymer that is a block polymer of poly-L-lactic acid and polycaprolactone and a second polymer is polycaprolactone;
    wherein the polymeric blend has a first melting point and a second melting point less than the first melting point; and
    wherein the medical device body is configured to be heat set to hold a shape at a temperature within 10° C. of the second melting point.

2. The medical device of claim 1, wherein the first block polymer includes about 60% or more of poly-L-lactic acid.

3. The medical device of claim 1, wherein the first block polymer includes about 70% or more of poly-L-lactic acid.

4. The medical device of claim 1, wherein the first block polymer is biodegradable.

5. The medical device of claim 1, wherein the one or more multi-melting point polymeric filaments are woven, knit, braided, or combinations thereof.

6. The medical device of claim 1, wherein the medical device body includes a plurality of multi-melting point polymeric filaments.

7. The medical device of claim 1, wherein the second melting point is in the range of about 50° C. to about 75° C.

8. A medical device, comprising:
    a medical device body formed from one or more multi-melting point polymeric filaments;
    wherein each of the filaments is formed of a polymeric blend of a biodegradable first block polymer that is a block polymer of poly-L-lactic acid and polycaprolactone and a second polymer is polycaprolactone;
    wherein the polymeric blend has a first melting point and a second melting point less than the first melting point and greater than 37° C.; and
    wherein the medical device body is configured to be heat set to hold a shape at a temperature within 10° C. of the second melting point.

9. The medical device of claim 8, wherein the second polymer is biodegradable.

10. The medical device of claim 8, wherein the first block polymer includes about 60% or more of poly-L-lactic acid.

11. The medical device of claim 8, wherein the second polymer comprises about 5% or more of the polymeric blend.

12. The medical device of claim 8, wherein the one or more multi-melting point polymeric filaments are woven, knit, braided, or combinations thereof.

13. The medical device of claim 8, wherein the medical device body comprises a stent.

14. A stent, comprising:
    a cylindrical body formed from a plurality of woven polymeric filaments;
    wherein each of the plurality of woven polymeric filaments is formed of a polymeric blend of a first block polymer that is a block polymer of poly-L-lactic acid and polycaprolactone and a second polymer is polycaprolactone;
    wherein the polymeric blend has a first melting point and a second melting point lower than the first melting point;

wherein the first block polymer comprises poly-L-lactic acid and polycaprolactone;
wherein the second polymer comprises polycaprolactone; and
wherein the cylindrical body is configured to be heat set into a radially expanded configuration at a temperature within 10° C. of the second melting point.

15. The stent of claim 14, wherein the first block polymer includes about 60% or more of poly-L-lactic acid.

16. The stent of claim 14, wherein the second polymer comprises about 5% or more of the polymeric blend.

17. The medical device of claim 1, wherein the first block polymer comprises 70% to 95% of a total weight of the polymeric blend, and wherein the second polymer comprises about 5% to about 30% of a total weight of the polymeric blend.

18. The medical device of claim 8, wherein the first block polymer comprises 70% to 95% of a total weight of the polymeric blend, and wherein the second polymer comprises about 5% to about 30% of a total weight of the polymeric blend.

19. The stent of claim 14, wherein the first block polymer comprises 70% to 95% of a total weight of the polymeric blend, and wherein the second polymer comprises about 5% to about 30% of a total weight of the polymeric blend.

* * * * *